United States Patent [19]
Winnek

[11] 3,962,579
[45] June 8, 1976

[54] THREE-DIMENSIONAL RADIOGRAPHY
[76] Inventor: Douglas Fredwill Winnek, 10450 W. Loyola Drive, Los Altos Hills, Calif. 94022
[22] Filed: Jan. 3, 1975
[21] Appl. No.: 538,425

Related U.S. Application Data
[63] Continuation of Ser. No. 447,108, Feb. 28, 1974, abandoned, which is a continuation of Ser. No. 273,653, July 20, 1972, abandoned.

[52] U.S. Cl. ............................ 250/313; 250/492 R
[51] Int. Cl.² ......................................... G01N 23/04
[58] Field of Search ..................... 250/313, 314, 492

[56] References Cited
UNITED STATES PATENTS

| | | | |
|---|---|---|---|
| 1,447,399 | 3/1923 | Pease | 250/60 |
| 2,029,300 | 2/1936 | Arfsten | 250/313 |
| 2,214,621 | 9/1940 | Leishman | 250/60 |
| 2,318,983 | 5/1943 | Winnek | 250/313 |
| 3,560,790 | 2/1971 | Tripp | 250/313 |
| 3,665,184 | 5/1972 | Schagen | 250/313 |
| 3,783,282 | 1/1974 | Hoppenstein | 250/313 |

*Primary Examiner*—Archie R. Borchelt
*Assistant Examiner*—B. C. Anderson
*Attorney, Agent, or Firm*—Townsend and Townsend

[57] ABSTRACT

Apparatus and a method for making an X-ray photograph of an object wherein the photograph, when viewed through a lenticular screen or other similar device, will provide a three-dimensional picture of the object and the interior parts thereof. The method is carried out by successively directing the X-ray beams from an elongated continuum of point sources of X-rays through the object, then through an improved parallax grating, and finally onto the film. The grating is formed of a plurality of spaced, generally parallel rods opaque to X-rays and extending transversely of said continuum to form a series of spaced slits through which the beams can pass onto the film, whereby the beams will form a series of side-by-side aspect views or images of the object on the film which can be viewed in three-dimension with the lenticular screen. Accurate measurements of depths of interior parts of the object can be made with the exposed film. A method of making the grating is also disclosed.

3 Claims, 6 Drawing Figures

THREE-DIMENSIONAL RADIOGRAPHY

This is a continuation of application Ser. No. 447,108 filed Feb. 28, 1974 now abandoned, the latter being a continuation of application Ser. No. 273,653, filed July 20, 1972 now abandoned.

This invention relates to improvements in X-ray diagnostic techniques and, more particularly, to apparatus and method for exposing a photographic film to X-rays in a manner to permit images on the exposed film to be viewed in three-dimension by means of a lenticular screen.

The conventional X-ray photograph merely shows a two-dimensional view of an object, such as a particular part of the human body. Such a two-dimensional view does not, in many cases, give a diagnostician adequate information as to the extent of a particular disorder, such as the depth of the foreign object in a body part or the displacement of a body part from its normal position. Thus, the use of such a two-dimensional X-ray photograph is limited and leaves many questions to be answered by the use of other techniques.

To overcome some of the problems associated with the use of standard two-dimensional X-ray film, the concept of tomography was developed to provide information which the conventional two-dimensional X-ray photograph was not capable of providing. Tomography is a technique of body section radiography in which both the source of X-rays (the X-ray tube) and the film holder are in motion during a particular exposure. However, the X-ray source and film holder move in opposite directions and the holder is on the opposite side of the object to be X-rayed from the source. The effect of tomography is to blur all images on either side of a particular flat plane so that objects in such plane, the focus of rotation, can be isolated from objects out of such plane. While the tomograph, i.e., the film resulting from the practice of tomography, represents an improvement over the conventional two-dimensional X-ray photograph, it is also limited as a diagnostic tool for several reasons. For instance, for optimal resolution, the desired X-ray tube motion should be such that it blurs all unwanted shadows. This can be achieved by a wide tube excursion and by projection of the X-ray beam through all angles of inclination during the exposure.

Although proper tube movement is essential, other factors also present problems in containing good image resolution. These include the fact that the X-ray equipment must be sufficiently rigid so as to be essentially free of vibration to prevent movement of the film holder during exposure. Also, proper exposure factors must be properly selected and a high frequency rotating anode for the X-ray tube must be provided with a fractional focal spot. Furthermore, extremely high-speed film is required to obtain the proper exposure. Finally, it is imperative that the object to be X-rayed, such as a patient, be completely immobilized during the exposure to assure that the focal point of the X-rays during transit of the X-ray source remain in a single plane.

Because of the foregoing requirements, tomography has been found to be of limited use as a diagnostic tool and gives rise to inaccuracies which render diagnoses questionable. For instance, a diagnostician cannot, in many cases, determine with accuracy the location and depth of a particular skeletal disorder when utilizing tomography inasmuch as the focal plane of the various X-ray beams may vary slightly during the entire exposure due to one reason or another, such as movement of the patient or vibration of the film holder relative to the patient.

The present invention is directed to an improvement in the use of photographs as diagnostic tools and is directed to apparatus and a method for obtaining a photograph of an object using electromagnetic radiation from a source, such as an X-ray tube, isotope or the like, in a manner to permit the film, when viewed through a lenticular screen, to reveal objects in three-dimension. Thus, not only can the film be viewed for specific size information but it can also be used for determining the specific depths in which certain objects are located relative to a predetermined reference so as to provide diagnostic information which has heretofore been unobtainable from any of the earlier X-ray photographic techniques. The electromagnetic radiation utilized in the present invention will hereinafter be referred to as X-rays, but is not limited thereto since any such radiation is suitable if it provides photographs which permit three-dimensional viewing as hereinafter described.

To carry out the foregoing, the present invention is directed to the provision and use of a parallax grating formed of a plurality of generally parallel rods opaque to X-rays, the rods being spaced apart sufficiently to permit X-ray beams, as they issue from a continuum of point sources, to pass between the rods and to form on the photogrraphic film behind the grating a plurality of aspect picture elements which are disposed in side-by-side relationship to each other and define linear slit images, there being one slit image behind each grating rod. The panoramic series of aspect views are laterally displaced in neat columns behind the rods and are separately placed upon the film emulsion in a plurality of juxtaposed positions.

After the exposed film has been properly developed, it can be used with a lenticular screen for viewing and the lenticular screen will be designed to project the spatial image into an angular field of observer space of a predetermined angle. Thus, upon viewing the picture through the lenticular screen, each eye of an observer sees its own respective aspect view and the observer will, therefore, see a particular stereo pair of picture elements so as to perceive an orthoscopic three-dimensional spatial image of the X-rayed objected from any viewing position within the angular field of view.

The present invention also permits the formation of an X-ray photograph which, in conjunction with the lenticular screen, can be used to determine depths of various objects or locations in the three-dimensional picture as viewed with the screen. Thus, it is possible not only to determine the size of a particular object which is X-rayed but also its depth to which the object is located with reference to other objects adjacent thereto.

The primary object of this invention is to provide apparatus and method for providing a photograph exposed to electromagnetic radiations in a manner such that the photograph, when viewed through a lenticular screen, permits objects to be viewed in three-dimension.

Another object of this invention is to provide apparatus and method of the type described wherein a photographic film is successively exposed to radiation beams from a continuum of point sources as the film remains stationary relative to said source continuum and as the beams scan transversely across a parallax grating in front of the film, whereby aspect views of the objects are recorded on the film in a manner to achieve a three-dimensional effect when viewed with the lenticular screen.

Another object of the present invention is to provide apparatus and a method of the type described wherein a parallax grating comprised of a plurality of parallel rods opaque to the radiation is disposed in front of the film and in the path of the radiation beams and between the object and the film so that the beams can pass through only the spaces between the rods to thereby assure that the film will be exposed to aspect views of the object which are laterally displaced in neat, linear picture elements.

Other objects of this invention will become apparent as the following specification progresses, reference being had to the accompanying drawings for an illustration of the invention.

Figure 1:
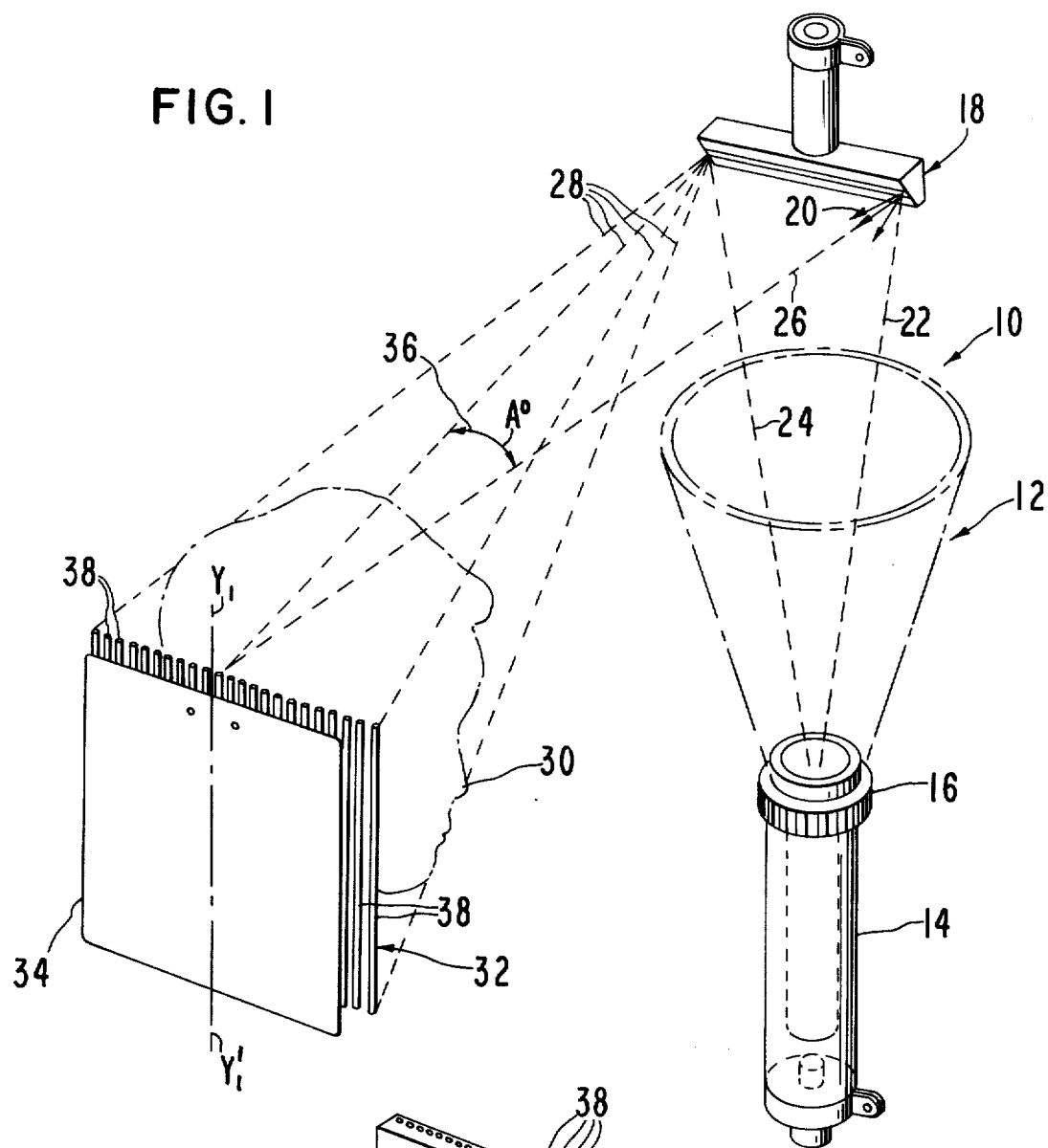
FIG. 1 is a perspective view of the apparatus for obtaining an X-ray photograph which can be used to view images in three-dimension, illustrating the grating of the invention schematically.
Figure 1B:
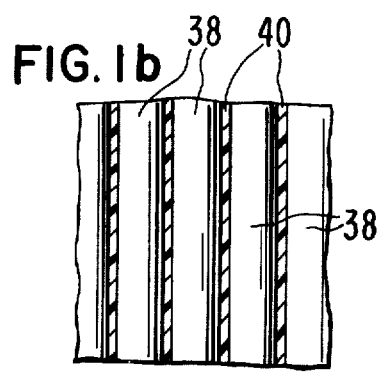
FIG. 1b is an enlarged, fragmentary, cross-sectional view of the grating.
Figure 1A:
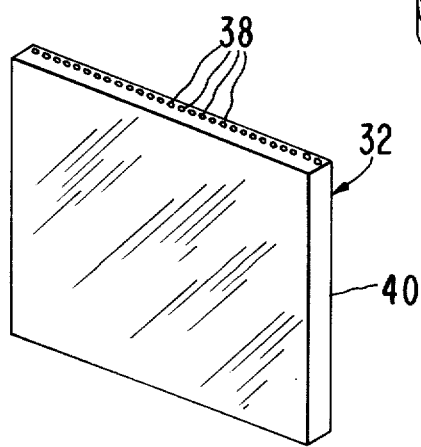
FIG. 1a is a perspective view of the grating on an enlarged scale, showing the way the rods thereof are embedded in a moldable support.

The apparatus for carrying out the method of this invention is illustrated in FIG. 1 and is denoted by the numeral 10. Apparatus 10 includes an X-ray tube 12 having an electron gun 14, a sweep coil 16 and a strip target 18 against which an electron beam from gun 14 is directed to generate X-ray beams denoted by the arrows 20. Strip target 18 defines an elongated continuum of point sources of the X-ray beams inasmuch as the electron beam scans the face of the target by means of sweep coil 16. For instance, dashed line 22 represents the beam at one extremity of target 18 and dashed line 24 represents the electron beam as it moves toward the opposite extremity of the target. The electron beam is successively directed to intermediate points on the fact of the target, although there is no representation of the electron beam in FIG. 1 with respect to such intermediate points.

X-rays are generated and are directed along paths represented by dashed lines 26 and 28, line 26 defining the X-ray beam generated when the electron beam passing along line 22 strikes the target and lines 28 representing the X-ray beam emanating from the target after an electron beam passes thereto along dashed line 24. The electron beam or stream is swept back and forth across the length of the strip target 18 in rapid successive cycles, at least one complete cycle during a radiographic exposure. At each point along target 18, the X-ray beam emanates therefrom toward an object 30 placed between a parallax grating 32 and target 18. The X-ray beams successively pass through object 30, through grating 32 and onto a photographic film 34 in back of grating 32. The numeral 36 represents the angular field between limiting X-rays directed along dashed lines 26 and 28. While one form of a continuum of point sources of X-rays has been described above, it is clear that other types of such a continuum can be used if desired. For instance, the X-ray source used with a conventional tomograph can be used as a part of apparatus 10 in place of X-ray tube as described. In such a case, the X-ray tube itself sweeps along a predetermined path and, at each point along such p a, the X-ray tube defines a point source of X-rays so that the tube itself, due to its movement, defines a continuum of point sources of X-rays.

Grating 32 includes a plurality of spaced, parallel, transversely circular rods 38 which are made of a material opaque to X-rays, such as lead or tungsten. These rods are fixed relative to each other such as by being embedded in a rigid panel 40 of a suitable moldable material, such as a thermoplastic resin or the like. Panel 40 may be formed of Formica, bakelite or other suitable material.

Each rod 38 can be of any desired diameter to achieve the aspect views of object 30 on film 34. For instance, rods 38 may be of a diameter of .022 inches and the spacing between each pair of adjacent rods can be approximately .003 inches. A suitable packing density of the rods is 40 per inch and a typical width of grating 32 is 14 inches. The diameter of the rods is selected so that the rods are sufficiently thick to be opaque to the X-ray beams. However, the material of panel 40 is transparent to X-ray beams; thus, the X-ray beams striking grating 32 pass through the same through the spaces between adjacent pairs of rods. The rods are located in a generally flat plane which is substantially parallel to the plane of film 34.

One way of forming grating 32 is to provide a metallic mold which is etched or scribed with a plurality of elongated grooves or recesses for receiving elongated, drawn wires or rods of lead or tungsten. Each groove may be V-shaped or transversely semi-circular so that each drawn wire can be properly seated in the mold. After all of the drawn wires are in respective grooves of the mold, a flowable mass of thermoplastic material, such as a resin, is poured onto the wires as they rest in the grooves of the mold. The thermoplastic material is allowed to set to a hardened condition and when properly cured, is removed from the mold with rods 38 embedded in one side face thereof. The grating is then ready for use and can be placed in a film cassette, specifically forming one closure for the cassette housing itself. The cassette, with the grating as a part thereof, can be loaded in the conventional manner so that the cassette can be put in a fixed position on a support (not shown) forming a part of apparatus 10. Thus, X-rays from tube 12 passing through object 30 will pass grating 32 and onto film 34 inasmuch as the cassette will be mounted on the support at a location to be disposed across the X-ray beams emanating from the continuum of point sources represented by target 18.

In use, X-rays emanate from target 18 successively from points along the length of the same and the X-rays pass toward and through object 30 and toward the plane of grating 32. The X-rays pass through the slits or spaces between adjacent pairs of rods 38 and the rods block other portions of the X-ray beams. Those X-rays that pass through the grating expose film 34 and provide aspect picture elements of object 30 thereon. Thus, the picture elements define linear slit images, one behind each rod 38. The panoramic series of aspect views are laterally displaced neatly in the aforesaid linear picture elements behind the rods and are separately placed on the film emulsion in juxtaposition to each other. The radiographic image on the film can be considered a parallax panoramagram and the film itself can be considered a parallax panograph.

Figure 2:
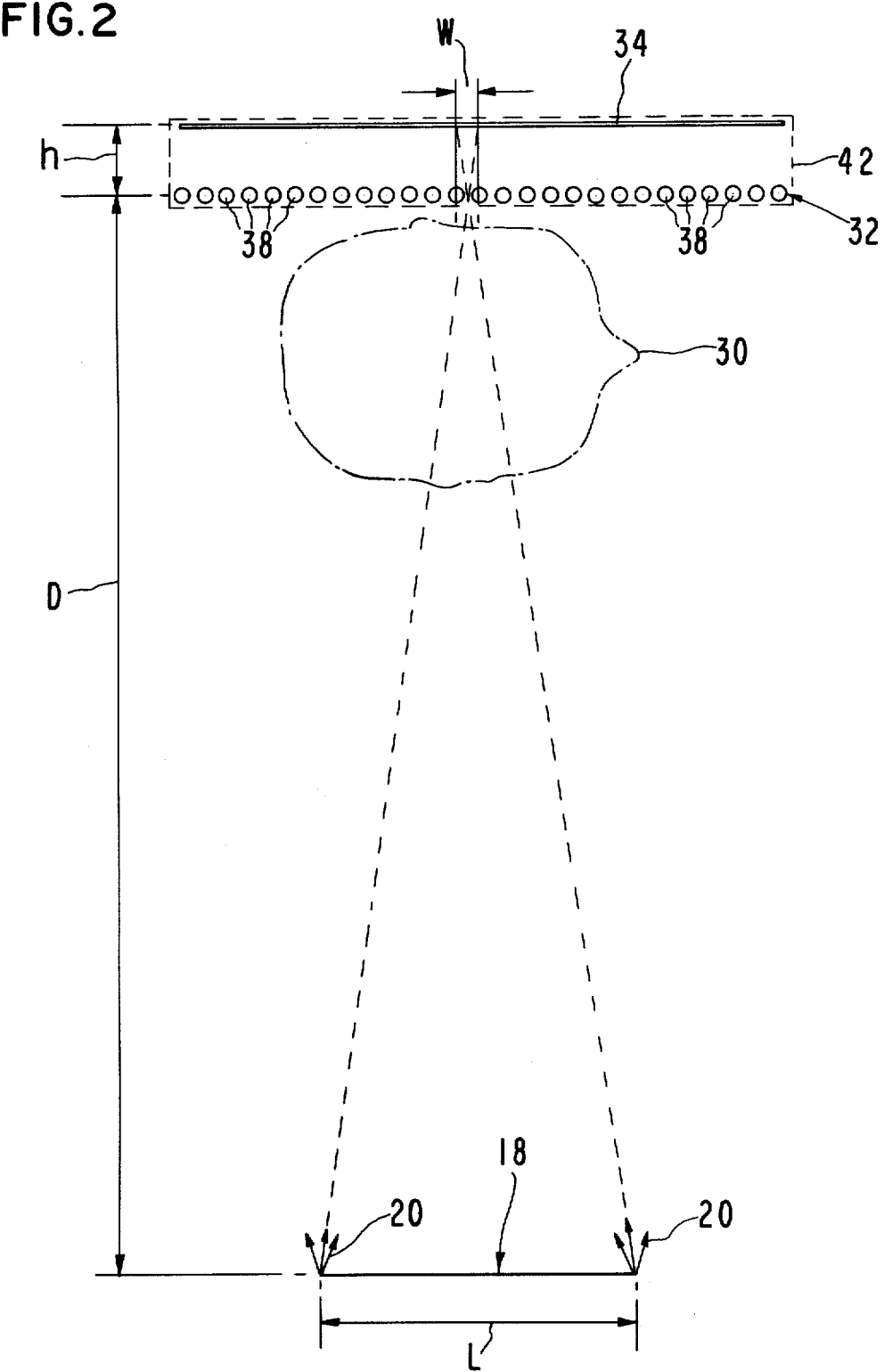
FIG. 2 is a top plan view of the system of FIG. 1, showing the grating schematically.

In FIG. 2, the radiographic system of this invention is shown in plan form along with specific parameters relating to the relative positions of the point source continuum, object 30, grating 32 and film 34. For instance, distance D between the strip target 18 and grating 32 is typically 90 centimeters and the length L of target 18 is typically 15 centimeters. Distance $h$ is measured between the emulsion of film 34 and the crossover plane of grating 32, such plane being measured through the center lines of rods 38. The distance $w$ represents the width of one emulsion area behind one rod and one clear space adjacent thereto.

Distance $h$ must be a specific value to assure that the emulsion behind one rod and one clear space is correctly "filled". The correct distance $h$ is given by the equation:

$$h = Dw/L.$$

The film cassette 42, shown only schematically in FIG. 2 houses grating 32 at the front thereof and film 34 near the back. The cassette should be equipped with a Kodak register pin calcium (with two pins) which can be cemented at the top of the X-ray film chamber. X-ray films punched with a Kodak register punch in the bright safe-light of the loading room will locate in a fixed relation to the grating when loaded in the cassette. Standard radiographic films are suitable for use in the cassette. Excellent radiographs for use in carrying out the present invention can be produced on the following films:

Kodak Industrial AA, Kodak type M, Gaevert Structured XX and many others. These films are double coated, i.e., coated on both sides of the film sheet. The film should be loaded firmly between calcium tungstate intensifying screens to assure maximum radiographic contrast.

Figure 3:
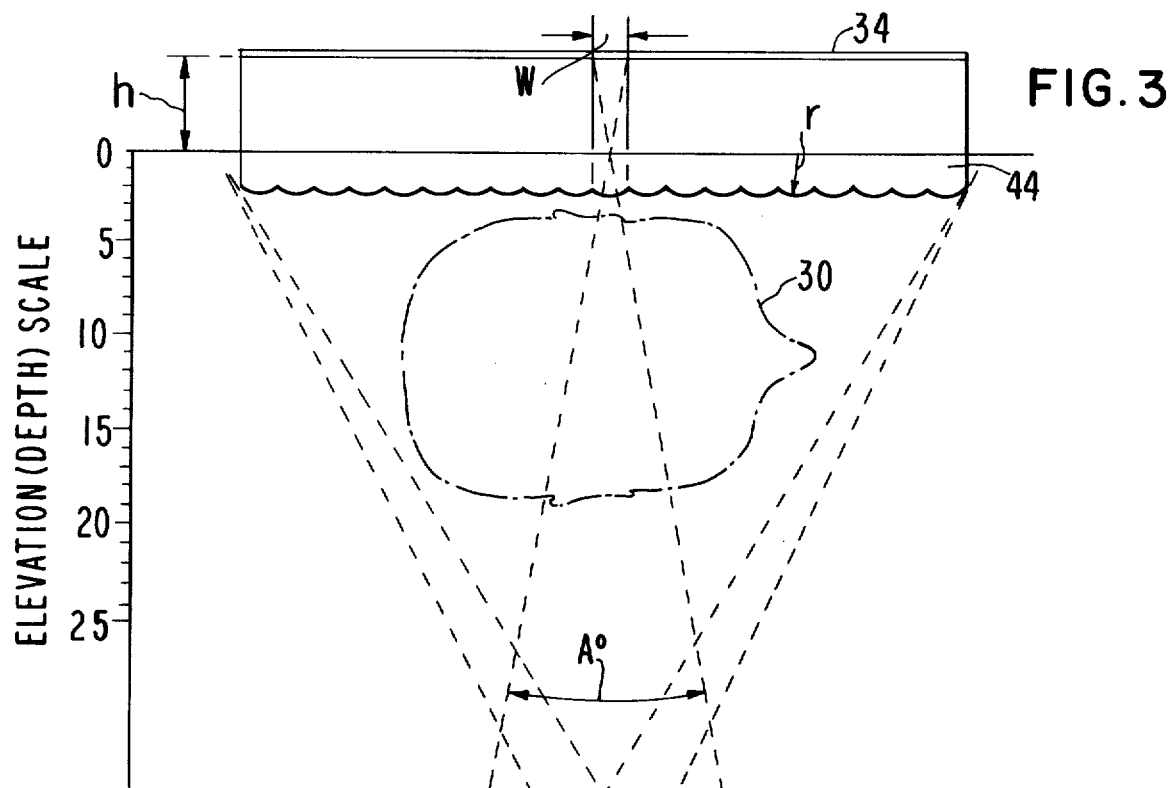
FIG. 3 is a view similar to FIG. 2 but showing the way in which the photographic film is viewed with a lenticular screen after the film has been exposed and processed.

After the film has been exposed and processed, it is viewed through a lenticular screen 44 which is placed in registry and held flat against the film surface for viewing. The film is held firmly against the flat window of an illuminator (not shown in FIG. 3). Screen 44 is designed to project the spatial image into an angular field of observer space of an arch angle of $A°$.

Upon viewing the picture through screen 44, each eye of an observer sees its own respective aspect view. Because the eyes are separated by the pupillary distance of about 2-⅜ inches, the observer will see a stereo pair of images and will perceive an orthoscopic three-dimensional spatial image of object 30 or some particular part thereof from any viewing position within the angular field of view. Depth planes of the spatial images commence at zero depth at the optical center of the lenticular screen and increase in even increments in the observer space to the nearest plane visible in the spatial image.

Screen 44 must be constructed so as to match the number of grating lines per inch (pitch) of grating 32 through which the X-ray beams pass. When energies of 30 KV to 120 KV are employed, the thickness of the grating may be essentially that of the diameter of each rod, for instance, 0.022 inches. Allowing for the adjacent clear space of 0.003 inches in width, grating $w$ (FIG. 3) will be approximately 0.025 inches and the grating pitch will be 40 lines per inch. In this case, the lenticular screen must also be 40 lines per inch.

The angular aperture ($A$) of each lens ridge of screen 44 is greater when the screen is thin or narrower when the screen is thick. A preferred angular aperture is $23°$. This will allow the viewer to move laterally in a field about three times wider than his pupillary separation when he is viewing from the closest (minimum) view point. He will see the spatial image in orthoscopic perspective when viewing from any desired viewing position within this angular observer space.

In summary, the parameters of lenticular screen 44 designed for use with the 40-line per inch parallax grating 32 are as follows:

Width of lens ridge ($w$) is .025 inches
Angular aperture ($A°$) is $23°$.
$h$ is equal to $2.5w$
$h$ is equal to $2r$ or $0.0625$ inches.

The refractive index of the material forming screen 44 is preferably about 1.5. Such material includes Acrylic, acetates, polystyrene, polychlorides and vinyls.

Figure 4:
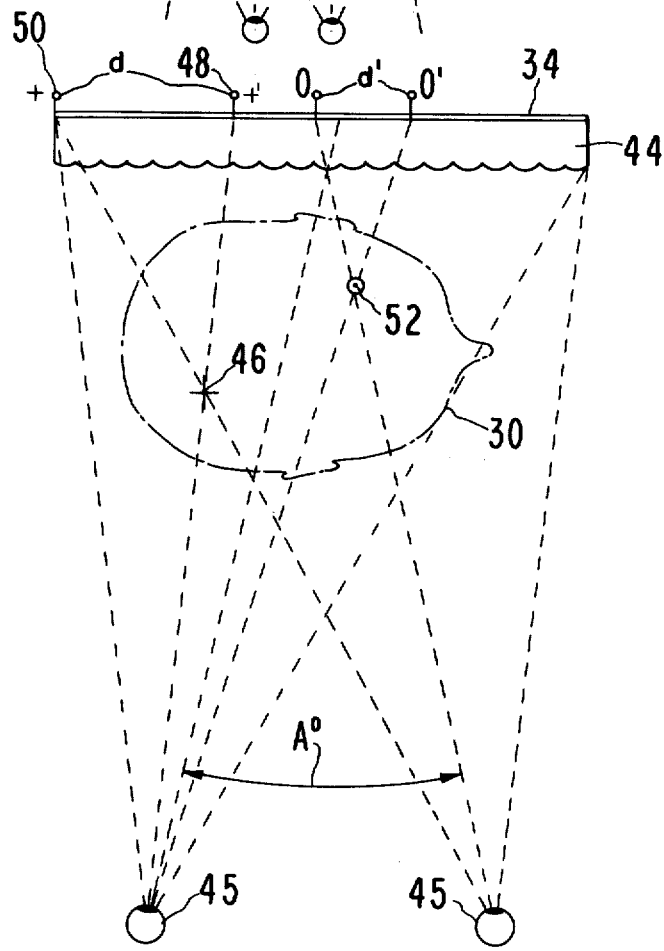
FIG. 4 is a view similar to FIG. 3 and showing the way in which depth dimensions can be made with the film.

FIG. 4 illustrates how "depth" measurements can be made utilizing film 34. For instance, when the film is viewed through screen 44 and as the viewer moves across the viewing field, from one side to the other, the image of a subject point is seen to move laterally across the film. When one eye 45 of the viewer is located at the left-hand position of FIG. 4, the viewer will see an object 46 imaged at position 48. When the eye 45 is at the right-hand position of FIG. 4, the viewer will see 46 imaged at position 50. Positions 48 and 50 are separated by a displacement $b$ and, regardless of the direction of movement of the eye right to left or left to right, displacement $b$ will always be the same.

When a grid line is pre-exposed on the film or is simply held against the film surface, the viewer can read displacement $b$ in the units of the grid line, for instance in millimeters. With reference to FIG. 2, when the viewer knows the values of grating distance D, target length L and displacement $d$ in millimeters, than the depth position of subject point 46 can be determined by the following equation:

(depth) $\delta$ equal $(D-\delta)d/L$

When D and L are held constant, displacement readings can be plotted against depth increments on a curve so that reference to such a curve readily confirms depth measurements obtained by using the last-mentioned equation.

FIG. 4 also shows that another object 52 having a greater depth than 46 will have a displacement $d'$ less than that of 46.

Due to perspective, the shadow of a structure increases in width directly with its depth position in the X-rayed object 30. The "real" width ($w_r$) of a structure is determined after its depth ($\delta$) is known by the equation:

$w_r = DW_0 D\text{-}\delta$, where $w_0$ is the measured shadow width of the structure.

I claim:

1. Apparatus for use in the exposure of a film for making a photograph of a three-dimensional object by X-ray radiation beams from a plurality of point sources of said radiation comprising: a grating including a support, and a plurality of parallel, spaced, transversely circular rods rigidly secured to said support, each rod being opaque to said radiation, said grating adapted to be positioned at a location between said point sources and said film to permit the beams from said sources to pass between said rods and onto the film, each rod presenting a first, elongated, convex surface to the incoming radiation from each point source, respectively, and a second elongated, convex surface opposite to the corresponding first surface and in facing relationship to said film when the grating is at said location.

2. Apparatus for making a photograph of a three-dimensional object at a predetermined location comprising: means providing a continuum of point sources of electromagnetic radiation on one side of said location with said sources adapted to be successively actuated to direct respective radiation beams emanating therefrom toward and through an object at said location; a film holder adapted to contain a photographic film sensitive to said radiation; means mounting the holder on the opposite side of said location with the holder being operable to maintain said film in an operative position across the paths of said beams; a grating coupled to the holder and disposed between said location and said film position, said grating including a plurality of transversely circular rods opaque to said radiation; and means mounting said rods in parallel, sapced relationship to each other with the rods being in a plane at a preselected distance from said film position, each rod presenting a first elongated, convex surface to the radiation from each point source, respectively, and a second elongated, convex surface opposite to the corresponding first surface and in facing relationship to said film position.

3. A method of obtaining a photograph of a three-dimensional object at a predetermined location comprising: providing a continuum of actuatable point sources of X-rays on one side of said location with said sources adapted to be successively actuated to direct respective X-ray beams emanating therefrom toward and through an object at said location; placing a photographic film sensitive to X-rays on the opposite side of said location and across the paths of the X-ray beams; placing a plurality of spaced, transversely circular X-ray opaque material between said film and the object with said regions being coplanar with each other and in a plane at a preselected distance from the film, each region presenting a first, elongated, convex surface to the X-rays from each source, respectively, and a second, elongated, convex surface opposite to the corresponding first surface and in facing relationship to said film; and successively actuating said X-ray sources to cause the beams emanating therefrom to be directed toward and through said object and through only the spaces between said regions.

* * * * *